United States Patent [19]

Hasson

[11] Patent Number: 4,935,006
[45] Date of Patent: Jun. 19, 1990

[54] SUCTION AND IRRIGATION DEVICE WITH RIGHT ANGLE AND OBLIQUE OPENINGS

[76] Inventor: Harrith M. Hasson, P.O. Box 14898, Chicago, Ill. 60614

[21] Appl. No.: 119,807

[22] Filed: Nov. 12, 1987

[51] Int. Cl.⁵ .............................................. A61M 3/00
[52] U.S. Cl. ...................................... 604/43; 604/268
[58] Field of Search .................. 128/750, 760; 604/43, 604/65, 264, 268, 280; 210/454

[56] References Cited

U.S. PATENT DOCUMENTS

| | | | |
|---|---|---|---|
| 3,735,751 | 5/1973 | Katz | 128/750 |
| 4,014,333 | 5/1977 | McIntyre | 604/43 |
| 4,158,916 | 6/1979 | Adler | 604/268 |
| 4,265,621 | 5/1981 | McVey | 604/268 |
| 4,418,702 | 12/1983 | Brown et al. | 128/760 |
| 4,573,979 | 3/1986 | Blake | 604/43 |
| 4,717,379 | 1/1988 | Ekholner | 604/43 |
| 4,755,175 | 7/1988 | Nilssen | 604/268 |

FOREIGN PATENT DOCUMENTS 2324374 12/1974 Fed. Rep. of Germany ...... 604/268

Primary Examiner—Max Hindenburg
Attorney, Agent, or Firm—Wood, Phillips, Mason, Recktenwald & Vansanten

[57] ABSTRACT

A suction device is provided having a tube connectable at its proximal end to a vacuum source and open at its distal end to provide suction at the distal end. A porous barrier is located within the tube distal end, being either a rigid screen filter or supporting a compressible filter which is drawn against the barrier by the tube vacuum. The filter alternatively may be secured to a housing which is securable to the tube distal end. The device further has a second tube disposed around the first tube, with the second tube being closed at opposite ends around the first tube to define an irrigation channel therebetween. The channel is connected to an irrigation source and has discharge openings at its distal end. The suction and irrigation functions of the channels can be reversed with the small openings in the outer channel defining a rigid screen during suction.

19 Claims, 2 Drawing Sheets

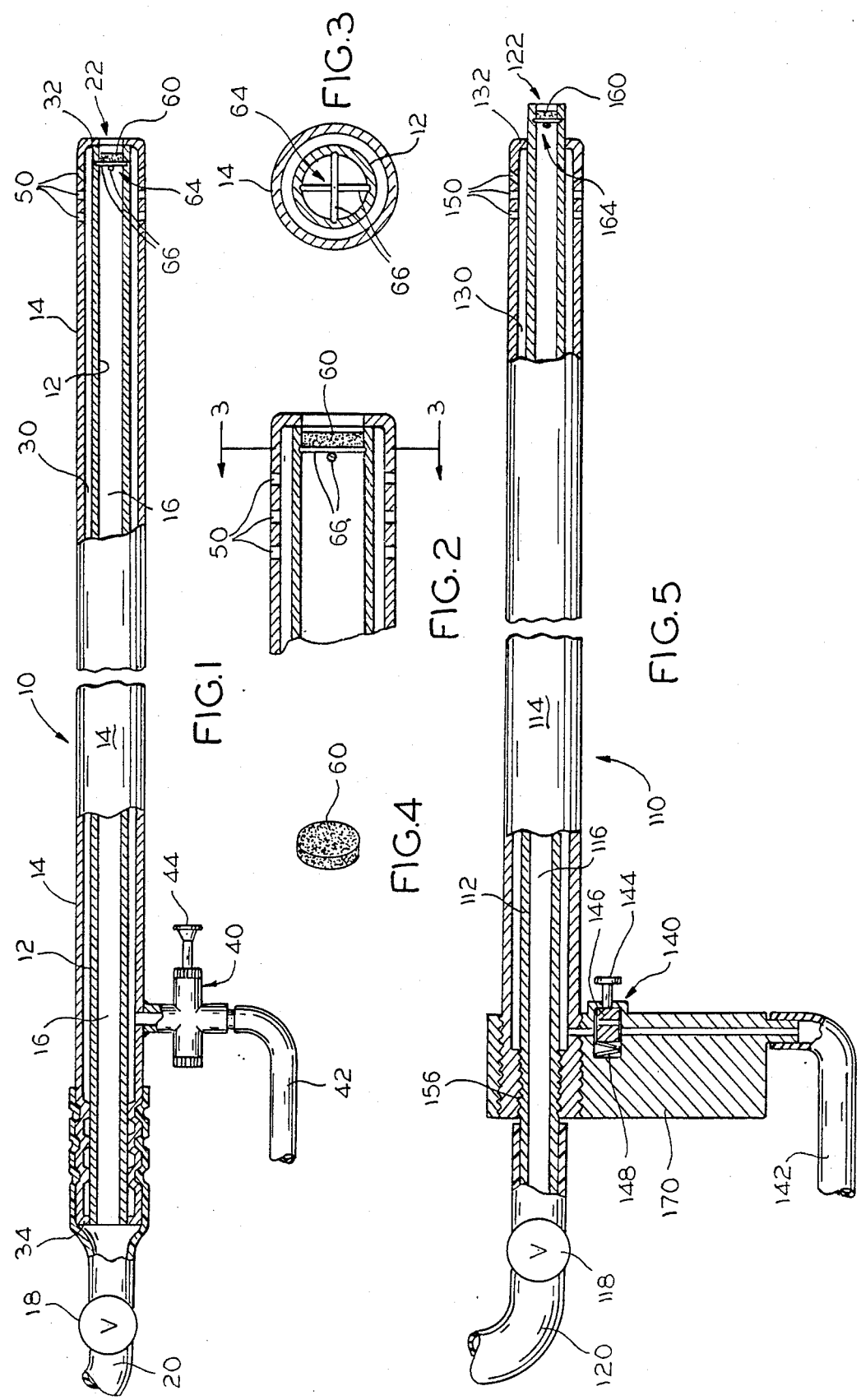

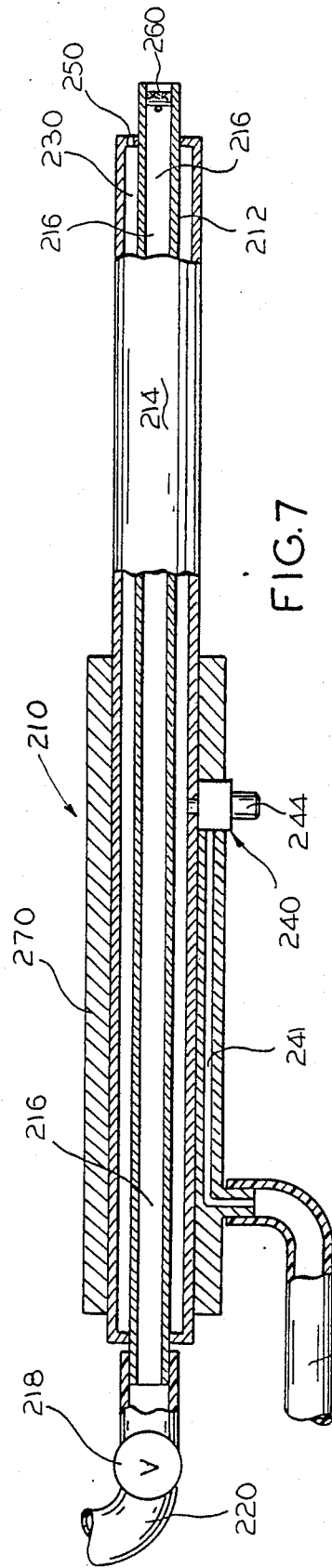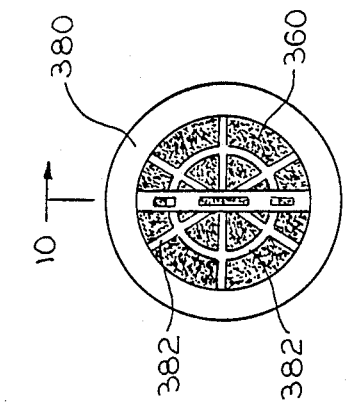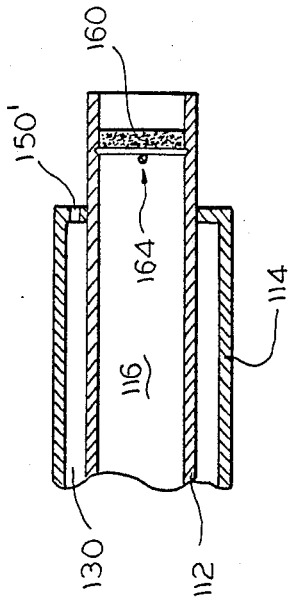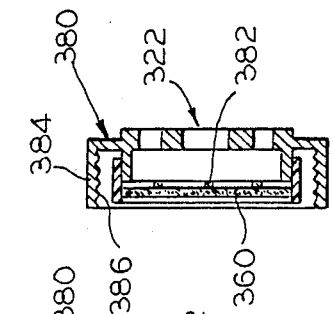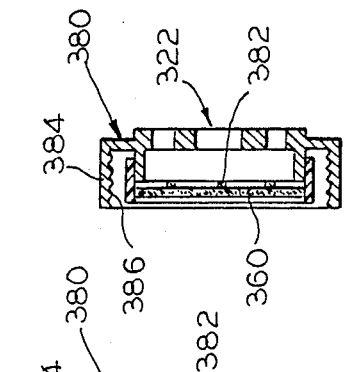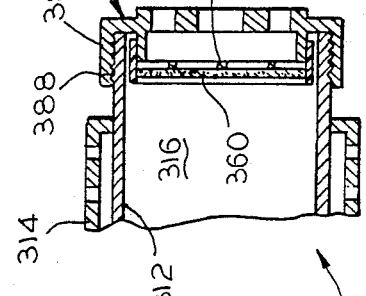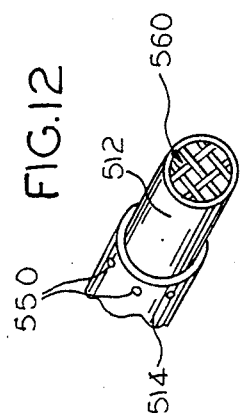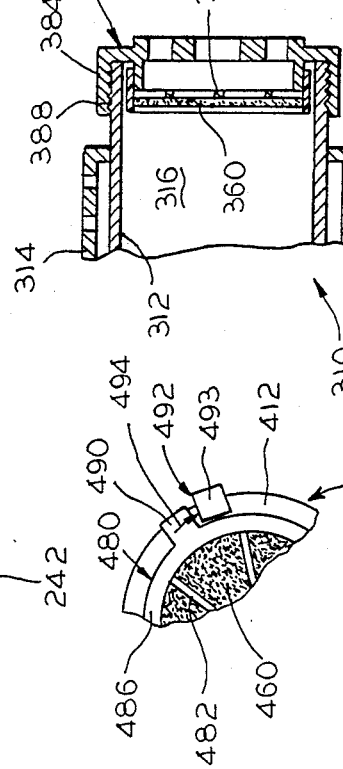

SUCTION AND IRRIGATION DEVICE WITH RIGHT ANGLE AND OBLIQUE OPENINGS

TECHNICAL FIELD

The present invention relates to surgical instruments, and more particularly to an instrument for providing suction and irrigation during surgery.

BACKGROUND ART

It is common in various surgical procedures to provide suction to the area of the surgery in order to remove blood and tissue which would hinder the surgeon's view. Similarly, irrigation by a saline solution is commonly provided to further help to ensure that the surgeon's view will be unhindered.

Suction and irrigation devices of the prior art have commonly been hand held instruments connected to a vacuum source, with suction provided continuously and irrigation provided only on demand (to prevent undesirable flooding of the surgical area).

Such devices have, however, sometimes clogged the suction tube with blood clots or tissue fragments, and entrapped bowel, omentum, oviduct and other tissues within the suction tube. Also, during laparoscopic uses (the possibilities of which have increased due to the recent introduction of laser modality), these problems are particularly aggravated by space limitations imposed by endoscopic modality. Still further, these devices commonly cause a noise during suction which can be irritating, adversely affecting the surgeon's concentration, and can interfere with communication among the surgical staff.

The present invention is directed toward overcoming one or more of the problems as set forth above.

SUMMARY OF THE INVENTION

In one aspect of the present invention, a suction device is provided having a tube connectable at its proximal end to a vacuum source and open at its distal end to provide suction at the distal end. Cross members are located within the tube distal end, and a compressible filter is drawn against the cross members by the tube vacuum.

In another aspect of the present invention, the filter is secured to a housing which is securable to the tube distal end.

In still another aspect of the present invention, the filter comprises a rigid screen fixed across the distal end of the tube.

In yet another aspect of the present invention, the device further provides for irrigation, having a second tube disposed around the first tube, with the second tube being closed at opposite ends around the first tube to define a channel therebetween. The channel is connected to an irrigation source and has discharge openings at its distal end.

It is an object of the present invention to minimize noise resulting from the suction device.

It is another object of the present invention to minimize clogging of the device and entrapment of tissue or other objects within the suction channel.

It is still another object of the present invention to provide a suction device which also conveniently allows for the introduction of irrigation when necessary.

Yet another object of the invention is to provide a suction and irrigation device which facilitates the required manipulations so that it can be easily and conveniently used in various different types of surgery.

Still another object of the present invention is to provide a suction and irrigation device which can be easily and inexpensively manufactured, while at the same time providing for reliable use.

BRIEF DESCRIPTION OF THE DRAWINGS

FIG. 1 is a partially cross-sectional view of one embodiment of the present invention;

FIG. 2 is an enlarged cross-sectional view of the distal end of the FIG. 1 embodiment;

FIG. 3 is a cross-sectional view taken along line 3—3 of FIG. 2;

FIG. 4 is a perspective view of a filter usable with the present invention;

FIG. 5 is a partially cross-sectional view of a second embodiment of the present invention;

FIG. 6 is an cross-sectional view of another embodiment of the distal end of the present invention;

FIG. 7 is a partially cross-sectional view of a third embodiment of the present invention;

FIG. 8 is a cross-sectional view of another embodiment of the distal end of the present invention, illustrating yet another structure for securing a filter thereto;

FIG. 9 is an end view of the filter and housing usable in the FIG. 8 embodiment;

FIG. 10 is a cross-sectional view taken along line 10—10 of FIG. 9;

FIG. 11 is an end view of yet another filter housing on the distal end of the suction and irrigation device; and FIG. 12 is a perspective view of still another filter structure which may be used on the distal end of the suction and irrigation device.

DESCRIPTION OF THE PREFERRED EMBODIMENTS

One embodiment of the suction and irrigation device 10 of the present invention is shown in FIG. 1. The device includes an inner stainless steel tube 12 and a concentric outer stainless steel tube 14.

The inner tube 12 defines a central channel 16 through which suction is drawn. The proximal end of the inner tube 12 has a suitable valve 18 which is connected to a vacuum source via a flexible hose 20 or the like. The valve 18 may be easily manipulated to stable open and closed positions. During surgery, the valve 18 may be opened so as to draw a constant vacuum through the central channel 16 to provide suction through the open distal end 22 of the inner tube 12.

The outer tube 14 is spaced from the inner tube 12 so as to define an outer channel 30 therebetween (which channel 30 is considerably narrower than the central channel 16). The outer tube 14 and the inner tube 12 are suitably connected at opposite ends (preferably by reducing the outer tube 14 diameter at its opposite ends as indicated at reference numerals 32 and 34) so as to effectively close the outer channel 30.

The connection of the inner and outer tubes 12, 14 can either be a fixed connection, or can be a proximity connection (with a hair line separation only). The latter connection provides an effective closing while allowing the tubes 12, 14 to be separated for ease of cleaning or the like. Thus, during surgery, one inner tube 12 may be removed and replaced with another inner tube 12 while the first tube is being cleaned.

A positive pressure valve 40 is also provided on the outer tube 14, connecting the outer channel 30 to a source of irrigation (such as saline solution) via another flexible hose 42 or the like. The valve 40 is normally closed, and opens only with the application of positive pressure on the activating button 44. When pressure on the button 44 is released, the valve 40 closes. Thus, irrigation is provided only while the button 44 is depressed.

Yet another positive pressure valve can also be provided with the inner tube 12 in place of the valve 18 shown, where desired, to facilitate use of both tubes 12, 14 interchangeably for suction and irrigation, as is further discussed below.

The outer tube 14 contains a plurality of irrigation discharge openings 50 at its distal end. These openings 50 are circumferentially spaced in annular array around the tube 14, with some of the openings 50 being at right angles to the tube axis and others being drilled obliquely into the outer tube 14 to direct irrigating streams obliquely forward. There are a plurality of arrays of openings spaced lengthwise of the tube 14. These openings 50 thus function as irrigation ports which spray a fine shower in several directions (either oblique or perpendicular to the direction of the suction in the central channel 16). This flow pattern is particularly appropriate for simultaneous irrigation and suction. In addition, irrigation is optimized by the combination of the relatively limited capacity of the outer channel 30 and the small size of the openings 50, which tend to increase the pressure of the irrigation shower.

A filter 60 is also provided at the distal end of the inner tube 12. A porous barrier or grid restraint 64 comprising cross members 66 suitably secured within the central channel 16 of the inner tube 12 mechanically supports the filter 60 so as to prevent it from being drawn up through the tube 12 by the suction therein (see particularly FIGS. 2-4).

The filter 60 is a thin cylindrical pellet of suitable porous material, typically less than 5 mm long and having a greater diameter than the central channel 16. Prior to surgery, the filter 60 may be introduced by using small tissue forceps, and it will remain in place due to both the suction and compression (since it has a larger diameter than the channel 16 within which it is located).

This small filter 60 reduces noise resulting from the suction without also undesirably decreasing the force of the suction provided by the device 10. In addition, the filter 60 protects the channel 16 from becoming clogged or trapping tissue or the like.

Of course, the filter 60 is readily disposable so that, following suction, blood clots and tissue can either be removed from the filter 60 or the filter 60 can be readily replaced using the small tissue forceps.

A second embodiment of the suction and irrigation device 110 is shown in FIG. 5 (with components being given the same reference numerals as similar components in the FIG. 1 embodiment, but increased by 100).

With this device 110, a pistol-type grip 170 is provided, with the flexible irrigation hose 142 connected to the end of the grip 170, and the valve 140 disposed in the grip 170 with its actuating button 144 located as a trigger. The valve 140 includes a valve member 146 biased outwardly by a compression spring 148 so that (like the FIG. 1 valve 40) it is normally closed, and open only when the valve button 144 is manually depressed.

In addition, this embodiment has a proximity connection between the inner tube 112 and the outer tube 114.

The hair line separation between the two tubes 112, 114 effectively closes the outer channel 130 so as to limit irrigation discharge to the openings 150, and also allows the tubes 112, 114 to be separated between uses for ease of cleaning or the like. A threaded connection 156 is provided between the inner and outer tubes 112, 114 to secure them together while also allowing easy separation for cleaning.

FIG. 6 illustrates the distal end of an alternative device usable when pin point irrigation is required. In this device, a small frontal irrigation opening 150' is provided which emits a fine single stream in the same plane as the suction. Such a fine stream of irrigation is commonly desirable in microsurgery.

Yet another embodiment of the invention is shown in FIG. 7 (with components being given the same reference numerals as similar components in the FIG. 1 embodiment, but increased by 200). With this device 210, a concentric handle 270 having an irrigation passage 241 and a valve 240 with an actuating button 244 is provided to allow the user to have yet another feel, allowing the device 210 to be easily manipulated during various types of surgery (as set forth further below).

Yet another structure for securing the filter 360 to the distal end of the tube 312 is shown in FIGS. 8-10. With this structure, the filter 360 is suitably secured to a filter housing or cartridge 380, as by gluing or otherwise mechanically connecting to a substantially open supporting cross structure or grid 382. The housing 380 may also have a suitable reinforcing grid at the distal end 322, which reinforcing grid must also be substantially open.

The filter housing 380 includes an annular flange 384 with an inner thread 386 which may be screwed onto an outer thread 388 on the distal end 322 of the inner tube 312. The filter housing 380, which may be made of a suitable inexpensive plastic material, can thus be cheaply, easily, and securely installed to the end of the device 310 whenever it is desirable to use a new filter 360.

This structure thus restrains the filter 360 from being sucked into the central channel 316 and also retains the filter 360, ensuring that the filter 360 does not inadvertently fall from the device 310 (which could, if not noticed, causes problems if left in a body cavity).

Still other housing structures for securely locating changeable filters over the distal end 322 of the inner tube 312 could also be used.

For example, as shown in FIG. 11, the filter housing 480 can be provided with a cap 486 having radial flanges 490 extending from the cap and receivable in radial slots 492 in axial lugs 493 on the tube distal end 422 when twisted in the direction of the arrow 494. Alternatively, the filter housing 480 could be tapered so that it could be suitably wedged into the open end of the inner tube 312 (or over the outer surface of the tube 312) so as to frictionally bind therein could be used.

In addition, a two piece housing could be used, with the filter secured to an inexpensive, disposable support which can be secured to a reusable cap, the cap being securable to the distal end of the device 310 by methods such as previously described and shown in FIGS. 8-11.

Still another embodiment of the present invention is shown in FIG. 12, where the filter 560 is a rigid screen which is suitably fixed on the end of the inner tube 512. Such a filter 560 will not be inadvertently lost in a patient during surgery, and can be easily cleaned by washing fluid through the inner tube 512, which is preferably removable from its associated outer tube.

Various combinations of the above features can be used for different types of surgery. For example, for microsurgery, a device having a filter either rigidly secured (such as shown in FIG. 12) or in a releasably lockable housing (such as shown in FIGS. 8-11), sealed tubes, one frontal hole (FIGS. 6 and 7), and the concentric tube type handle (FIG. 7) would probably be best used.

Alternatively, for laparoscopic surgery, a device having a filter either rigidly secured or in a releasably lockable housing, separable tubes, multiple side irrigation discharge openings (FIGS. 1, 2 and 5), and the basic valve irrigation connection (FIG. 1) would be suitable. For standard (macro) surgery, a similar device but with the gun type handle (FIG. 5) would probably be best used.

Of course, a basic device having only suction with the filter secured therein as described could also be used in standard surgery where only suction is required.

In addition, a skilled artisan will recognize that the channels 16, 30 may be interchangeably used for irrigation and suction as desired. For example, the central channel 16 will be conventionally used for suction and the outer channel 30 for irrigation. However, by changing the connection of the hoses 20, 42 to the valves 18, 40, both channels 16, 30 may simultaneously be used for suction, or both may be used for irrigation, or the central channel 16 may be used for irrigation with the outer channel 30 simultaneously used for suction. In this case, the small openings in the outer channel would define a rigid screen filter. (Of course, if the inner channel 16 is used for irrigation, inadvertent discharge of the filter 60 into the body cavity must be guarded against. Where such a use is anticipated, filters 360 secured by a housing 380 or 480 such as shown in FIGS. 8-11 would be particularly useful in avoiding such inadvertent mistakes, as would rigid secured screen filters 560 such as shown in FIG. 12.)

Of course, either or both channels 16, 30 could also be used for gas insufflation or evacuation.

The suction and irrigation device 10 of the present invention will thus minimize noise resulting from suction, thereby allowing the surgical staff to concentrate and communicate fully. The device 10 will also not become clogged during use by tissues or membranes since only filtered fluids pass through the central channel 16 or outer channel 30. Further, the device 10 may be conveniently used in different types of surgery, allowing for use of various handles and various options for simultaneous suction and/or irrigation and/or gas insufflation or evacuation.

Still further, the device 10 may be used to collect cells and tissue fragments for subsequent analysis.

Other aspects, objects and advantages of the present invention can be obtained from a study of the drawings, specification, and appended claims.

I claim:

1. A suction and irrigation device for use in surgery and adapted for connection to a vacuum source and an irrigation source, comprising:
    a first tube connectable at its proximal end to the vacuum source and open at its distal end to provide suction at said distal end;
    a second tube having a lengthwise axis disposed around said first tube to define an outer channel therebetween, said first and second tubes being closed together at opposite ends to close the channel ends;
    means for discharging fluid irrigation from the outer channel at the distal end of the device,
    said discharging means comprising a plurality of openings in the second tube, said openings being arranged in annular arrays, there being at least first and second annular arrays spaced lengthwise of said second tube,
    there being a first plurality of said openings extending obliquely through said second tube with respect to the length thereof so that fluid directed through said first plurality of openings is directed at other than a right angle to the axis of the second tube and a second plurality of said openings extend through the second tube so that fluid directed through the second plurality of openings is directed at a right angle with respect to the second tube axis whereby the first and second plurality of openings cooperatively cause a random fluid discharge that showers the area around said second tube; and
    means for connecting said outer channel to the fluid irrigation source.

2. The suction and irrigation device of claim 1, wherein the discharging means comprises one frontal opening.

3. The suction and irrigation device of claim 1, further comprising porous barrier means fixed within the distal end of the first tube.

4. The suction and irrigation device of claim 3, wherein said barrier means comprises a rigid screen fixed to the first tube distal end.

5. The suction and irrigation device of claim 3, further comprising a compressible filter within the first tube distal end, said filter being drawn against the barrier means by the vacuum.

6. The suction and irrigation device of claim 1, further comprising:
    a filter secured to a cylindrical housing; and
    means for securing said housing to the first tube distal end.

7. The suction and irrigation device of claim 6, wherein said securing means comprises an annular flange with an inner thread receivable over a threaded portion on the distal end of the device.

8. The suction and irrigation device of claim 7, wherein said filter housing comprises:
    a disposable cylindrical support to which the filter is secured; and
    a reusable cap having the annular flange and being securable over the support to secure the filter within the first tube distal end.

9. The suction and irrigation device of claim 8, wherein said cap includes a cylindrical portion which is received within the cylindrical support and is tapered to frictionally bind the support between the cap and the inner surface of the tube distal end.

10. The suction and irrigation device of claim 6, wherein said securing means comprises:
    a set of circumferentially spaced slots in said first tube distal end; and
    a set of radial flanges on said housing receivable within said slots.

11. The suction and irrigation device of claim 10, wherein said filter housing comprises:
    a disposable cylindrical support to which the filter is secured; and a reusable cap having the radial flanges and being securable over the support to secure the filter within the first tube distal end.

12. The suction and irrigation device of claim 11, wherein said cap includes a cylindrical portion which is received within the cylindrical support and is tapered to frictionally bind the support between the cap and the inner surface of the tube distal end.

13. The suction and irrigation device of claim 1, wherein the connecting means comprises a valve on the second tube communicating with an opening through said second tube to the outer channel.

14. The suction and irrigation device of claim 13, further comprising:
   means for biasing said valve to a closed position; and
   means for manually opening said valve.

15. The suction and irrigation device of claim 14, further comprising a handle secured to the second tube in a gun configuration, wherein the opening means is positioned as a trigger on said handle.

16. The suction and irrigation device of claim 1, wherein the closure of the first and second tubes is a fixed connection.

17. The suction and irrigation device of claim 1, wherein the closure of the first and second tubes is a proximity connection.

18. The suction and irrigation device of claim 1 wherein a plurality of said openings extend obliquely through said second tube with respect to the length thereof and a plurality of said openings extend through the second tube perpendicular to the length of the second tube so as to cooperatively produce a shower in several directions.

19. The suction and irrigation device according to claim 1 wherein each opening in said first plurality of openings is defined by a cylindrical bore through the second tube and the axes for the first plurality of openings are transverse to the axis of the second tube.

* * * * *